United States Patent [19]

Callingham et al.

[11] Patent Number: 5,177,068
[45] Date of Patent: Jan. 5, 1993

[54] PHARMACEUTICAL COMPOSITIONS

[75] Inventors: Brian A. Callingham, Cambridge; Robert C. Hider, Clacton; George Kontoghiorghes, London; Michael A. Stockham, Saffron Walden, all of England

[73] Assignee: National Research Development Corporation, London, England

[21] Appl. No.: 349,964

[22] Filed: May 8, 1989

Related U.S. Application Data

[63] Continuation of Ser. No. 178,758, Mar. 30, 1988, abandoned, which is a continuation of Ser. No. 723,277, Apr. 15, 1985, abandoned.

[30] Foreign Application Priority Data

Apr. 19, 1984 [GB] United Kingdom ............. 8410289

[51] Int. Cl.⁵ .................. C07F 15/02; A61K 31/555; C07D 213/69; C07D 309/40
[52] U.S. Cl. .................. 514/184; 514/188; 514/814; 546/6; 549/210
[58] Field of Search ................. 514/184, 188

[56] References Cited

U.S. PATENT DOCUMENTS

| | | | |
|---|---|---|---|
| 2,429,096 | 10/1947 | Ladd et al. | 167/33 |
| 2,686,786 | 8/1953 | Shaw et al. | 261/294.8 |
| 2,742,476 | 10/1953 | Bernstein et al. | 260/294.8 |
| 3,281,366 | 10/1966 | Judge et al. | 252/107 |
| 3,810,752 | 5/1974 | Wilcox et al. | 71/94 |
| 3,864,334 | 2/1975 | Pallos | 424/263 |
| 3,928,616 | 12/1975 | Pallos | 424/263 |
| 3,968,118 | 8/1975 | Lohaus et al. | 424/263 |
| 4,018,907 | 4/1977 | Scarpellino | 426/250 |
| 4,018,934 | 4/1977 | Parliment | 426/250 |
| 4,063,927 | 12/1977 | Otten et al. | 71/74 |
| 4,181,654 | 1/1980 | Weitl et al. | 424/244 |
| 4,225,614 | 9/1980 | Hansson | 424/289 |
| 4,279,936 | 7/1981 | Jones et al. | 426/265 |
| 4,293,542 | 10/1981 | Lang et al. | 424/47 |
| 4,309,305 | 1/1982 | Weitl et al. | 252/631 |
| 4,315,942 | 2/1982 | Corden | 424/297 |
| 4,358,455 | 11/1982 | Atkinson et al. | 546/300 |
| 4,396,766 | 8/1983 | Farmer, Jr. et al. | 546/6 |
| 4,397,867 | 8/1983 | Blake | 424/230 |
| 4,419,365 | 12/1983 | McLachlan | 424/320 |
| 4,442,305 | 4/1984 | Weitl et al. | 562/451 |
| 4,530,963 | 7/1985 | DeVoe et al. | 525/54.1 |
| 4,543,213 | 9/1985 | Weitl et al. | 564/142 |
| 4,550,101 | 10/1985 | Hider | 514/188 |
| 4,575,502 | 3/1986 | Hider | 514/184 |
| 4,585,780 | 4/1986 | Hider et al. | 514/348 |
| 4,587,240 | 5/1986 | Hider | 546/6 |
| 4,650,793 | 3/1987 | Hider | 514/188 |
| 4,698,431 | 10/1987 | Raymond et al. | 546/261 |

FOREIGN PATENT DOCUMENTS

| | | |
|---|---|---|
| 0094149 | 11/1983 | European Pat. Off. . |
| 0107458 | 5/1984 | European Pat. Off. . |
| 0120670 | 10/1984 | European Pat. Off. . |
| 2613500 | 10/1976 | Fed. Rep. of Germany . |
| 2130M | 4/1985 | France . |
| 162003 | 7/1964 | U.S.S.R. . |
| 761171 | 11/1956 | United Kingdom . |
| 1377006 | 12/1974 | United Kingdom . |
| 2117766 | 10/1983 | United Kingdom . |
| 2118176 | 10/1983 | United Kingdom . |
| 2128998 | 5/1984 | United Kingdom . |
| 2136806 | 9/1984 | United Kingdom . |
| 778871 | 7/1987 | United Kingdom . |

OTHER PUBLICATIONS

Chemical Abstracts: 97:92048a (1982) Bartulin et al.
Merck Index (1976) 9th Edition, Merck & Co., Inc., Rahway, N.J. 543-544.
Chemical Abstracts: 94:156749c (1981) Shin-Etsu Chemical Industry Co. Ltd.
Chemical Abstracts: 98:71930n (1983) Harada, Rokuro.
Manufacturing Chemist & Aerosol News (May 1970) E. Jones.
Pharmaceutical Dosage Forms, vol. 3 (1982) Marcel Decker, pp. 165-167 Lieberman & Lachman.
Chemical Abstracts: 75:115362k (1971) Kidani et al.
Chemical Abstracts: 94:41144j (1981) Kimura et al.
Chemical Abstracts: 94:24201h (1981) Gerard et al.
Yaku Gaku Zasshi, 90 (10), 1222-1225, Yasue et al., "Synthesis from Maltol . . . ", (1970) and translation.
Chemical Abstracts, 1976, 85, 56109q, Katyal et al., "2,3-Dihydroxypyridine . . . ".

(List continued on next page.)

Primary Examiner—Mark L. Berch
Attorney, Agent, or Firm—Nixon & Vanderhye

[57] ABSTRACT

Iron complexes comprising a ferric cation in combination with at least two different ligands, at least one of which is provided by a compound being:

(1) 3-hydroxy-4-pyrone or a 3-hydroxy-4-pyrone in which one or more of the hydrogen atoms attached to ring carbon atoms are replaced by an aliphatic hydrocarbon group of 1 to 6 carbon atoms; or (2) a 3-hydroxypyrid-2-one or 3-hydroxypyrid-4-one in which the hydrogen atom attached to the nitrogen atom is replaced by an aliphatic acyl group, by an aliphatic hydrocarbon group of 1 to 6 carbon atoms, or by an aliphatic hydrocarbon group substituted by one or more substituents selected from aliphatic acyl, alkoxy, alphatic amide, aliphatic ester, halogen and hydroxy groups and, optionally, in which one or more of the hydrogen atoms attached to ring carbon atoms are replaced by one of said substituents, by an aliphatic hydrocarbon group of 1 to 6 carbon atoms, or by an aliphatic hydrocarbon group substituted by an alkoxy, aliphatic ester, halogen or hydroxy group; the charge on the ferric cation being neutralized by the charge on the ligands covalently bound thereto; are of value in medicine, particularly in the treatment of iron deficiency anaemia.

19 Claims, No Drawings

OTHER PUBLICATIONS

Talanta, 1974, 21, 763–769, Kushwaha et al., "Complexation reactions of pyridinols".

Chemical Abstracts, 1985, 102, 124493g, Scarrow et al., "Ferric ion sequestering agents . . . ".

"Symposium on Development of Iron Chelators for Clinical Use", Anderson & Hiller (Eds.), 1975, pp. 137–173, (Sept. 22, 1975).

Chem. Pharm. Bull., 1980, 28, 2570–2579, Kumira et al., "Central Depressant Effects of Maltol Analogs in Mice".

J. Chem. Res. (M), 1980, 3919–3927 paper F/016/80, Gerard et al., "Complexes ferriques du maltol . . . ".

Pfizer Technical Bull., 1974, Data Sheet No. 04/A, "Veltol".

Pfizer Technical Bull., 1974, No. 865 & 867, "Veltol and Veltol Plus".

Coll. Czech. Chem. Commun., 1968, 33, 4198–4214, Stefanovic et al., "On the reaction of iron(III) with maltol".

J. Coord. Chem., 1978, 8, 27–33, Habeeb et al., "Direct electrochemical synthesis of some metal chelate complexes".

J. Chem. Res. (S), 1980, 314, Gerard et al., "Iron complexes of maltol . . . ".

Nagoya Shiritsu Daigaku Yakugakubu Kenkyu Nempo, 1970, 18, 16–21 Kidani et al., "Synthesis of maltol-Fe(III) complex" (and translation).

Report of Iron Uptake from FeIII maltol, Jan. 1986, Maxton, Thompson & Hilder, "Human Studies".

Letter from University of Kansas Medical Center, Feb. 14, 1986, Skikne.

"Study to compare the effect of iron maltol versus ferrous sulphate in the correction of chronic iron deficiency anaemia", 1986, Blake.

Struct. Bonding (Berlin), 1984, 58, 25–87, Hider, "Siderophore Mediated Absorption of Iron".

Chemical Abstracts, 1981, 94, 24201h, Gerard et al., "Iron(III) complexes of maltol . . . ". This is an abstract in English of item 15 which is in French.

Journal of Pharmacy and Pharmacology, 1954, 6, 1037–1047, Johnson & Thomas, "The Stability of Aqueous Solutions of Ferrous Gluconate".

Buckingham et al., J. Chem. Soc., Chem. Comm. 1982, pp. 779–781.

Anderson et al., Journal of Inorganic Biochemistry, 1982, vol. 16, pp. 21–32.

Anderson, Ed, *Symposium Proceedings*, Bethesda, Md. (1975) pp. 137–173.

Ward, *Aust. J. Biol. Sci.*, 1976, 29, pp. 189–196.

Tamhina, *Croatica Chemica Acta* CCACAA, 1973, 45, pp. 603–610.

Mentas, *Ann. Chim.*, (Rome), vol. 66, Nos. 7–8, 1976, pp. 401–415.

Howlin, CA 97:173875v, (1982).

Mentasi, CA 87:157681s, (1976).

Bidiel, *J. Chem. Soc., 69:1801 (1947)*.

Wilhaut, *Helvetica Chimica Acta*, vol. XXIX, fasciculus XII (1946), pp. 1669–1675.

Mohrle, *Tetrahedron* (1970), vol. 26, pp. 3779–3785.

Akera, *J. Bacteriology*, (Jan. 1980) vol. 141, No. 1, pp. 164–168.

Stunzi, *Aust. J. Chem.* (1979), 32, pp. 21–30.

Itoh et al., "The Journal of Antibiotics", vol. XXXII, No. 11, pp. 1089–1095 (Nov. 1979).

Barker et al., Journal of Antibiotics, vol. 32, No. 11, 1979, pp. 1096–1103.

McInnes et al., Journal of the Chemical Society, Chemical Communications, 1974, No. 8, 281–282. This paper relates to two pigment compounds which contain . . .

Neilands, Science, 1967, 156, 1443–1447.

Dittmar et al., J. Med. Chem., 1974, 17, 753–576. This paper describes a structure-activity analysis in a series of antimycotically active 1-hydroxypyrid-2-ones. The . . .

Durbin, P. W. et al., "Kinetics of Plutonium Deposition in the Mouse," Ann. Rpt. 1983-4, Biology and Medicine Division, Lawrence Berkeley Lab. (Apr. 1985) . . .

Durbin, P. W. et al., "New Sequestering Agents for the Actinides . . . ," Ann. Rpt. 1983-4, Biology and Medicine Division, Lawrence Berkeley Lab. (Apr. 1985) . . .

Raymond, K. N., "Specific Sequestering Agents for Iron and Actinides," in Environmental Inorganic Chemistry (VCH Publishers, Inc. 1985).

PHARMACEUTICAL COMPOSITIONS

This application is a continuation of application Ser. No. 07/178,758, filed on Mar. 30, 1988, now abandoned, which is a continuation of application Ser. No. 06/723,277, filed on Apr. 15, 1985, now abandoned.

BACKGROUND OF THE INVENTION

1. Field of the Invention

This invention relates to iron compounds for use in pharmaceutical compositions for the treatment of iron deficiency anaemia.

2. Discussion of the Background

An adequate supply of iron to the body is an essential requirement for tissue growth in both man and animals. Although there is normally an ample amount of iron in the diet, the level of absorption of iron from food is generally low so that the supply of iron to the body can easily become critical under a variety of conditions. Iron deficiency anaemia is commonly encountered in pregnancy and may also present a problem in the newly born, particularly in certain animal species such as the pig. Moreover, the certain pathological conditions there is a mal distribution of body iron leading to a state of chronic anaemia. This is seen in chronic diseases such as rheumatoid arthritis, certain haemolytic diseases and cancer.

Although a wide range of iron compounds is already marketed for the treatment of iron deficiency anaemia, the level of iron uptake by the body from these compounds is often quite low, necessitating the administration of relatively high dosage levels of the compound. The administration of high dose, poorly absorbed, iron complexes may cause siderosis of the gut wall and a variety of side effects such as nausea, vomiting, constipation and heavy malodorous stools.

In the UK patent applications of numbers (a) 8308053 (published as GB 2117766A), (b) 8327612 (published as GB 2128998A) and (c) 8407180 (published as GB 2136806A), and in corresponding applications filed the USA: (a) U.S. application Ser. No. 478,494 granted as U.S. Pat. No. 4,550,101 (b) U.S. applications Ser. Nos. 542,976 (granted as U.S. Pat. No. 4,575,502), 601,485 and 717,660, and (c) U.S. application Ser. No. 592,543); we describe iron complexes of various 3-hydroxpyrid-2-ones, 3-hydroxypyrid-4-ones and 3-hydroxy-4-pyrones which we have identified as being of particular value for use at relatively low dosage levels in the treatment of iron deficiency anaemia. It has now been found that certain advantages, as discussed hereinafter, accrue from the use of complexes not described in these earlier applications which contain one or more hydroxypyridone or hydroxypyrone ligands but in which the ligands present in the complex are not identical.

SUMMARY OF THE INVENTION

According to the present invention an iron complex comprises a ferric cation in combination with at least two different ligands, at least one of which is provided by a compound being:

(1) 3-hydroxy-4-pyrone or a 3-hydroxy-4-pyrone in which one or more of the hydrogen atoms attached to ring carbon atoms are replaced by an aliphatic or alicyclic hydrocarbon group of 1 to 6 carbon atoms; or (2) a 3-hydroxypyrid-2-one or 3-hydroxypyrid-4-one in which the hydrogen atom attached to the nitrogen atom is replaced by an aliphatic or alicyclic acyl group, by an aliphatic or alicyclic hydrocarbon group, or by an aliphatic or alicyclic hydrocarbon group substituted by one or more substituents selected from aliphatic or alicyclic acyl, alkoxy, aliphatic or alicyclic amide, aliphatic or alicyclic ester, halogen and hydroxy groups and, optionally, in which one or more of the hydrogen atoms attached to ring carbon atoms are replaced by one of said substituents, by an aliphatic or alicyclic hydrocarbon group, or by an aliphatic or alicyclic hydrocarbon group substituted by an alkoxy, aliphatic or alicyclic ester, halogen or hydroxy group; the trivalent positive charge on the ferric cation being neutralised by the charge on the ligands covalently bound thereto.

DETAILED DESCRIPTION OF THE PREFERRED EMBODIMENTS

It should be appreciated that a feature of the iron complexes of the present invention is that they are neutral, i.e. there is an internal balance of charges between the ferric cation and the ligands bound covalently thereto, there being no need for any additional non-covalently bound anion or anions, such as chloride, to balance the charge on the ferric cation. The hydroxypyridone and hydroxypyrone ligands are each bidentate and monobasic (the ligand containing a group -O- in place of the group -OH present in the compound itself). It is preferably the case that the iron complex is a 3:1 ligand:iron(III) complex which contains three monobasic, bidentate ligands, of which at least two are different, the ligands each separately being provided by a compound being:

(1) 3-hydroxy-4-pyrone or a 3-hydroxy-4-pyrone as defined hereinbefore;

(2) a 3-hydroxypyrid-2-one or 3-hydroxypyrid-4-one as defined hereinbefore; and (3) an alternative compound providing a physiologically acceptable, monobasic, bidentate ligand which is capable of bonding covalently to iron;

but with the proviso that at least one of the ligands is of type (1) or (2).

It will be appreciated that the 3:1 ligand:iron complexes of the present invention may contain various different combinations of the ligands of the types (1) to (3) described above, subject to the requirement that at least one is a hydroxypyridone or hydroxypyrone ligand and that a least two of the three ligands are not identical. Thus, all of the ligands may be of type (1) or of type (2), although differing within these types, or the ligands may be of all three types. Alternatively, the ligands may be a mixture of types (1) and (2), a mixture of types (1) and (3) or a mixture of types (2) and (3). It will most usually be the case that two of the monobasic, bidentate ligands present in a 3:1 complex will be the same, with the third one being different. Moreover, at least two will preferably be of the hydroxypyridone or hydroxypyrone type. Most conveniently, therefore, the complex contains three ligands of type (2) or particularly of type (1) which are derived from two different compounds, or the complex contains two identical ligands of type (2) or particularly of type (1) together with a third ligand which is either of type (1) or (2), respectively, or less preferably of type (3).

The ability of both the metal-free ligand-providing compounds and of the iron complex to permeate membranes is important in the context of the treatment of iron deficiency anaemia and it is also desirable for both to possess some degree of water solubility. A good indication of the physical properties of a ligand-providing compound and of an iron complex in this respect is provided by the value of the partition coefficient ($K_{part}$) obtained on partition between n-octanol and tris hydrochloride (20 mM, pH 7.4; tris representing 2-amino-2 hydroxymethylpropane 1,3-diol) at 20° C. and expressed as the ratio (concentration in organic phase)/(concentration in aqueous phase). Preferred complexes show a value of $K_{part}$ for each ligand-providing compound of above 0.02 or 0.05 but less than 3.0, especially of above 0.2 but less than 1.0, together with a value of $K_{part}$ for the 3:1 iron(III) complex of above 0.02 but less than 6.0, especially of above 0.1 or 0.2 but less than 1.0. For examples of measured partition coefficients of metal-free hydroxypyridones and hydroxypyrones, and of iron complexes thereof in which all of the ligands are identical, reference should be made to Example 1 of each of the three applications referred to hereinbefore. The following comments upon preferences among the different ligands of types (1) to (3) which may be used in complexes according to the present invention are made in the light of these preferences as to partition coefficients.

The hydroxypyrone ligands of type (1) are of particular value and the complexes according to the present invention may conveniently contain at least one such ligand. The substituted 3-hydroxy-4-pyrones may carry more than one type of aliphatic or alicyclic hydrocarbon group but this is not usual and, indeed, substitution by two rather than three, and particularly by only one aliphatic or alicyclic hydrocarbon group is preferred. The aliphatic or alicyclic (i.e. acyclic or cyclic respectively) hydrocarbon groups may have a branched chain or especially a straight chain in the case of aliphatic groups, and may be unsaturated or especially saturated. Groups of from 1 to 4 carbon atoms and particularly of 1 to 3 carbon atoms are of most interest. Alkyl groups are preferred, for example cyclic groups such a cyclopropyl and especially cyclohexyl but, more particularly preferred are acyclic alkyl groups such as n-propyl and isopropyl, and especially ethyl and methyl. Substitution at the 2-or 6-position is of especial interest although, when the ring is substituted by the larger aliphatic or alicyclic hydrocarbon groups, there may be an advantage in avoiding substitution on a carbon atom alpha to the

system. This system is involved in the complexing with iron and the close proximity of one of the larger aliphatic or alicyclic hydrocarbon groups may lead to steric effects which inhibit complex formation.

Preferred hydroxypyrones providing ligands present in complexes according to the present invention have the formula (I), specific hydroxypyrones of particular interest having the formulae (II) and (III):

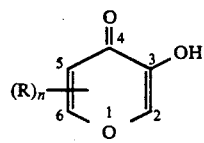
(I)

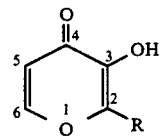
(II)

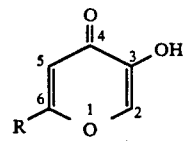
(III)

in which R is an alkyl group, for example methyl, ethyl, n-propyl isopropyl or butyl, and n is 0, 1, 2 or 3 (the ring being unsubstituted by any alkyl group when n is 0). Among these compounds 3-hydroxy-2-methyl-4-pyrone (maltol; II, R=CH₃) is of most interest, whilst 3-hydroxy-4-pyrone (pyromeconic acid; I, n=0) 3-hydroxy-6-methyl-4-pyrone (isomaltol; III, R=CH₃) and particularly 2-ethyl-3-hydroxy-4-pyrone (ethylpyromeconic acid; II, R=C₂H₅) are also of especial interest.

As regards the hydroxypyridone ligands of type (2), these may be derived from hydroxypyridones of the type described in UK Patent Application No. 8308053, published as GB 2117766A (U.S. Pat. No. 4,550,101) or of the type described in UK Patent Application No. 8407180, published as GB 2136806A (U.S. application Ser. No. 592,543 now U.S. Pat. No. 4,650,793) and claiming priority from UK Patent Application No. 8308055. The former consist of a 3-hydroxypyrid-2-one or 3-hydroxypyrid-4-one in which the hydrogen atom attached to the nitrogen atom is replaced by an aliphatic or alicyclic hydrocarbon group of 1 to 6 carbon atoms and, optionally, in which one or more of the hydrogen atoms attached to ring carbon atoms are also replaced by the same or a different aliphatic or alicyclic hydrocarbon group of 1 to 6 carbon atoms, whilst the latter consist of a 3-hydroxypyrid-2-one or 3-hydroxypyrid-4-one which is substituted as defined under (2) hereinbefore but excluding those compounds in which the replacement of hydrogen atoms is effected only by aliphatic or alicyclic hydrocarbon groups (these compounds being the substituted hydroxypyridones of the former application). Hydroxypyridones providing ligands which may be used in complexes according to the present invention have the formulae (IV) and (V)

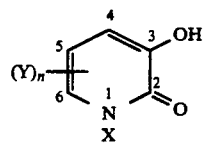
(IV)

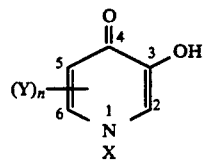
(V)

in which X is the substituent attached to the nitrogen atom as defined in paragraph (2) in the Summary of the Invention above and Y is the substituent attached to ring carbon atoms as defined in paragraph (2) in the Summary of the Invention, and n is 0, 1, 2 or 3, the 3-hydroxypyrid-2-ones generally being of somewhat greater interest than the 3-hydroxypyrid-4-ones.

Preferences as to the nature and position of the substituent groups present in the hydroxypyridones are broadly as expressed in the two earlier applications. Thus, substituted aliphatic or alicyclic hydrocarbon groups present in the hydroxypyridones may as indicated carry more than one substituent group but it is preferred that two rather than three, and particularly only one substituent group is present. Such substituted aliphatic or alicyclic hydrocarbon group substituents may conveniently contain groups of 1 to 8 and particularly of 1 to 6 carbon atoms, but the simpler hydroxypyridones of UK Patent Application GB 2117766A containing only unsubstituted aliphatic or alicyclic hydrocarbon group substituents are of the greatest interest. The preferences among the aliphatic or alicyclic hydrocarbon groups present in these hydroxypyridones correspond largely to those expressed in relation to the hydroxypyrones, with methyl groups conveniently being used for substitution on ring carbon atoms but larger alkyl groups also being of particular interest for substitution on the ring nitrogen atoms. Substitution of the ring carbon atoms, which is again preferably by one rather than two or three aliphatic or alicyclic hydrocarbon groups, is of particular interest in the case of the 3-hydroxypyrid-4-ones, for example at the 6- or particularly the 2-position, whilst the 3-hydroxypyrid-2-ones may more often be used without any additional aliphatic or alicyclic hydrocarbon group substituent on the ring carbon atoms. Specific hydroxypyridones of particular interest have formulae (VI), (VII), and (VIII)

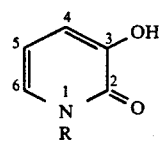
(VI)

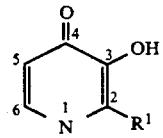
(VII)

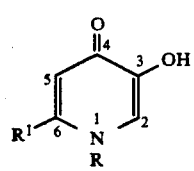
(VIII)

in which R is an alkyl group, for example methyl, ethyl, n-propyl, isopropyl or butyl, and $R^1$ is hydrogen or particularly an alkyl group, for example methyl. Among such compounds 1-ethyl-3-hydroxypyrid-2-one, 3-hydroxy-1-propylpyrid-2-one, 3-hydroxy-1-(1'-methylethyl)-pyrid-2-one, 1-butyl-3-hydroxypyrid-2-one, 1-ethyl-2-methyl-3-hydroxypyrid-4-one, 2-methyl-1-propyl-3-hydroxypyrid-4-one, 3-hydroxy-2-methyl-1-(1'-methylethyl)-pyrid-4-one and 1-butyl-3-hydroxy-2-methylpyrid-4-one are of particular interest with the 3-hydroxypyrid-2-ones such as 1-ethyl-3-hydroxypyrid-2-one being especially preferred.

The ligands of type (3) may be derived from various forms of compound, many of which are naturally occurring, and include physiologically acceptable, monobasic, bidentate ligands known in the art. The compounds which provide such ligands will generally comprise (a) a first grouping containing an acidic proton which is lost to provide both the single negative charge on the ligand and also one of its chelating sites and (b) a second grouping which provides the second chelating site. The grouping (a) is preferably either an enolic hydroxy group or a carboxy group whilst the grouping (b) is preferably an amino group, conveniently a primary amino group, or a hydroxy group. In a particular case, one grouping can fulfil both function (a) and function (b). Thus, some monocarboxylic acids can provide an anion capable of a bidentate mode and containing a grouping

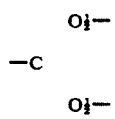

which will fulfil both functions.

Apart from such monocarboxylic acids, for example formic acid, propionic acid and particularly acetic acid, many other forms of acid are of interest for providing type (3) ligands. These include various hydroxy acids, for example lactic acid, gluconic acid, etc., and various amino acids, for example glycine, isoleucine, leucine, methionine, phenylalanine, tyrosine and valine. Also of interest are peptides, particularly the smaller compounds such as tri- and especially di-peptides, for example those containing the same or different amino acids selected from those listed above such as glycyl-leucine, leucyl-glycine and especially glycyl-glycine and leucyl-leucine. Apart from the carboxylic acids, the other group of compounds of particular interest is those containing a grouping

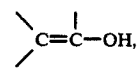

a particular example of this class being ascorbic acid (vitamin C). It should be noted that ascorbic acid is capable of providing a dibasic rather than a monobasic anion but compounds such as this are quite suitable for use in providing ligands of type (3) where they have a single pKa, only, which is less than 10 since, in use under physiological conditions, the ascorbate or other such anion will be monobasic. It will be appreciated from the foregoing discussion that the carbohydrate compounds gluconic acid and ascorbic acid are of interest in providing type (3) ligands and this interest extends to other carbohydrates, including particularly the monosaccharide sugars and related compounds. In selecting carbohydrate or other compounds for providing type (3) ligands, the more hydrophobic compounds are generally of greater interest so that among the amino acids, for example, the more complex amino acids than glycine may be of greater value.

Examples of specific iron complexes according to the present invention are (1-ethyl-3-hydroxypyrid-2-one)$_2$ (1-butyl-3-hydroxypyrid-4-one) iron(III), (maltol)$_2$ (1-ethyl-3-hydroxypyrid-2-one) iron(III), (maltol)$_2$ (leucine) iron(III), (maltol)$_2$ (glycine) iron(III), (maltol)$_2$ (ascorbic acid) iron(III), (maltol)$_2$ (gluconic acid) iron- (III) and especially (maltol)$_2$ (ethylpyromeconic acid) iron(III) and (ethylpyromeconic acid)$_2$ maltol iron(III). It will be appreciated that "maltol" is used in the names of these complexes to represent the ligand derived from maltol, and similarly for the other ligands, this usage being employed throughout the specification.

The iron complexes are conveniently prepared by the reaction of a mixture of the compounds which provide the ligands and iron ions, the latter conveniently being derived from an iron salt, particularly a ferric halide and especially ferric chloride. The reaction is conveniently effected in a suitable mutual solvent and water may be used for this purpose. If desired, however, an aqueous/organic solvent mixture may be used or an organic solvent, for example ethanol, methanol or chloroform and mixtures of these solvents together and/or with water where appropriate. In particular, methanol or especially ethanol may be used where it is desired to effect the separation of at least a major part of a by-product such as sodium chloride by precipitation whilst the iron complex is retained in solution.

The nature of the product obtained will depend in part upon the molar proportion of the various reactants but also upon the pH of the reaction medium. Thus, to prepare the ferric complexes containing a 3:1 molar proportion of ligand:iron(III), the ligand-providing compounds and the ferric salt are conveniently mixed in solution in a 3:1 molar proportion and the pH adjusted to a value in the range of 6 to 9, for example 7 or 8. If a similar excess of the compounds:iron is employed but no adjustment is made of the acidic pH which results on the admixture of the compounds and an iron salt such as ferric chloride, then a mixture of 2:1 and 1:1 complexes will instead be obtained. Adjustment of the pH may conveniently be effected by the addition of sodium carbonate as described hereinafter in Example 1. However, a possible alternative, which is of particular interest when preparing the iron complexes in batches of 20 g or more, is to use a hydroxide base such as sodium or ammonium hydroxide. When using a hydroxide base, the reaction may conveniently be carried out in 4:1 v/v ethanol:water as a solvent and the pH adjusted by the addition of a 2 molar aqueous solution of the base. It will be appreciated that the presence of a proportion of water in the reaction mixture will lead to the retention of a by-product in the iron complex on evaporation of the solvent (a chloride where the iron salt is ferric chloride). However, this can be removed, if desired, by procedures such as crystallisation from a suitable solvent system or sublimation in the particular case of ammonium chloride.

The individual ligand providing compounds may conveniently be used in a 1:1:1 or 2:1 molar proportion, with a 1 molar proportion of the ferric salt, depending on whether all three of the ligands are different or, as is usually preferred, two of the ligands are the same and the third is different. It will be appreciated, however, that the use of such proportions will not lead exclusively to the 1:1:1 or a single 2:1 complex since, although these forms of complex will predominate providing the ligand-providing compounds are of similar reactivity, they will be obtained in admixture with other forms of complex as discussed hereinafter. Indeed, if it is desired to enhance the degree of admixture of different forms of complex which is obtained, the proportions of reactants may be varied to this end. Thus, for example a 1.5:1.5 molar proportion of two different ligands may be used to encourage the formation of a mixture of the two possible types of 2:1 complex differing in the ligand which predominates.

Reaction to form the iron complex is generally rapid and will usually have proceeded substantially to completion after 5 minutes at about 20° C. although a longer reaction time may be used if necessary. Following separation of any precipitated by-product, such as sodium chloride in the case of certain solvent systems, the reaction mixture may conveniently be evaporated on a rotary evaporator to yield the iron complex which will usually be an oil initially which will, however, often form a glass on standing. The present invention thus further includes a process for the preparation of an iron complex as described hereinbefore, which comprises reacting a mixture of selected hydroxypyridone, hydroxypyrone and alternative ligand-providing compounds, as described hereinbefore, with ferric ions and isolating the resultant complex.

Whilst for some uses it may be appropriate to prepare the iron complex in a form free from by-products of manufacture apart from other complexes, in other cases, for example with a solid oral formulation as described hereinafter, the presence of by-products such as sodium chloride may be quite acceptable. In general, however, the neutral 3:1 iron(III) complex is of particular interest in a form which is substantially free at least from those by-products which are complexes containing different overall proportions of ligand:iron. Thus the 3:1 complex, although usually obtained and used in a form in which it is in admixture with other types of 3:1 complex as discussed hereinafter, is preferably substantially free from 2:1 and 1:1 complexes. In addition, the isolation of the complex will usually provide it in a form substantially free from any metal-free compound corresponding to a ligand present in the complex. The term "substantially free from" is used herein to indicate the presence of 10% by weight or less of the material referred to.

Certain of the ligand-providing compounds, such a maltol, are available commercially. With others, routes for their preparation are described in the three UK patent applications referred to hereinbefore. Thus, for example, with the hydroxypyrones a convenient starting material in many instances consists of pyromeconic acid which is readily obtainable by the decarboxylation of meconic acid and may be reacted with an aldehyde to insert a 1-Hydroxyalkyl group at the 2-position, which group may then be reduced to produce a 2-alkyl-3-hydroxy-4-pyrone. The preparation of 2-ethyl-3-hydroxy-4-pyrone, etc., by this route is described in U.S. application Ser. No. 310,141 (series of 1960).

It will be appreciated that these are not the only routes available to these compounds and their iron complexes and that various alternatives may be used as will be apparent to those skilled in the art. Moreover, it will be appreciated that certain of the compounds may be converted in vivo to other compounds which are responsible for the metal binding activity observed in vivo. This will be true, for example, of compounds containing ester groups which are likely to be converted to carboxy groups when the compounds are administered orally.

The iron complexes of the present invention are of particular interest for several reasons. Firstly, the inclusion in a complex of a mixture of different ligands provides an added dimension to the design of complexes having optimised properties for take up in vivo to provide a controlled supply of iron applicable in a particular human or veterinary context. More specifically, comparative results obtained in human erythrocytes and in non-everted rat jejunal segments suggest that complexes containing mixed ligands may provide a more available source of iron than iron complexes in which the ligands are homogeneous. Secondly, apart from the behaviour of the complexes in vivo, the present invention provides particular advantages in relation to the formulation of iron complexes. In certain contexts, as discussed in more detail hereinafter, liquid formulations of the iron complexes are of particular interest, for example for oral veterinary administration and particularly for parenteral veterinary and human administration, and it has been found that for use in such contexts the solubility of some of the iron complexes of the three previously mentioned UK patent applications is less than might have been desired.

The mixed ligand complexes of the present invention generally show much higher solubilities, both in water and in organic solvents, as compared with those in which the ligands are homogeneous. It is believed that the reason for this lies in the diversity of different stereoisomers of one complex which can arise when a mixture of ligands is present and which can be augmented by the presence of several different complexes in a reaction mixture obtained from the reaction with iron ions of more than one ligand producing compound. Thus, a 3:1 iron(III) complex containing three identical asymmetric ligands can exist in four stereoisomeric forms but when a complex is produced by the reaction of a 3 molar proportion of a mixture of two ligand-producing compounds (A and B) with ferric ions then the following types of complex may be present in the reaction mixture: $FeA_3$, $FeB_3$, $FeAB_2$ and $FeB_2A$. Moreover, although the first two mentioned complexes will exist in four stereoisomeric forms, the last two mentioned complexes will each exist in eight stereoisomeric forms (an even more complex mixture will result if three different ligands are present). It has been found that the four stereoisomers of a $FeA_3$ or $FeB_3$ complex will co-crystallise with ease but that for a $FeAB_2$ or $FeB_2A$ complex the increased number of steroisomers, and the presence of other 3:1 ligand:iron(III) complexes, prevents such co-crystallisation and ensures that the product is a liquid with enhanced solubility as compared with the usually solid $FeA_3$ and $FeB_3$ complexes.

The iron complexes according to the present invention may be formulated for use as pharmaceuticals for both veterinary, for example in an avian or particularly a mammalian context, and human use by a variety of methods. For instance, they may be applied as an aqueous, oily or emulsified composition incorporating a liquid diluent which may often be employed for parenteral administration and therefore may conveniently be sterile and pyrogen free. Oral administration is often preferred for the treatment of iron deficiency anaemia in humans and the complexes of the present invention may be given by such a route. Although compositions incorporating a liquid diluent may be used for oral administration, it is more usual, at least in humans, to use compositions incorporating a solid carrier, for example a conventional solid carrier material such as starch, lactose, dextrin or magnesium stearate. Such solid compositions may conveniently be of a formed type, for example as tablets, capsules (including spansules), etc.

Although solid compositions may be preferred for the treatment of iron deficiency anaemia in certain contexts, liquid compositions are of interest in other contexts, for example in human and veterinary intramuscular administration and in veterinary oral administration as discussed hereinafter. It is in the area of liquid compositions that the present invention is of particular, although certainly not exclusive, interest. Thus, it is often desirable to produce liquid compositions containing a higher concentration than is readily obtainable with a purely aqueous composition or indeed one containing organic solvents such as simple monohydric alcohols. It has been found with the iron complexes described in the three UK patent applications mentioned hereinbefore that higher concentrations may be achieved by the use of solvents containing two or more hydroxy groups or a hydroxy and an ether group, especially glycols or glycol ethers, either in admixture with water or, for better solubilisation, alone. The glycol ethers of particular interest are the mono-ethers containing as an etherifying group an aliphatic or alicyclic hydrocarbon group of 1 to 6 carbon atoms as described above, for example a methyl group, such a glycol monoether being methyl ethylene glycol. In general, however, the glycols themselves are preferred. Examples of such glycols are the simple dihydroxy alkanes such as ethylene glycol as well as those more complex compounds comprising two hydroxy groups attached to a chain containing both carbon and oxygen atoms, such as triethylene glycol, tetraethylene glycol and polyethylene glycol, for example of 4000 daltons molecular weight. Triethylene glycol and especially tetraethylene glycol are of particular interest in view of their very low toxicity. By using such glycols and glycol ethers it is possible to increase solubility for many complexes to 10 to 20 mg/ml. Although such techniques may also be employed in the formulation of the iron complexes according to the present invention their greater solubility will often allow one with advantage to employ simpler forms of liquid composition and still achieve concentrations considerably in excess of this 10 to 20 mg/ml range.

As indicated, liquid compositions are of particular interest in relation to parenteral administration, a requirement for which arises with humans in certain contexts but also particularly in a veterinary context, for example with pigs. The problems of iron deficiency anaemia in newly born pigs arise primarily during the first three weeks or so of their life when a very rapid weight gain takes place. The usual routes for administration of the iron complexes of the present invention to young piglets are parenteral, for example intramuscular, or oral, for example as a liquid preparation "injected" into the mouth. However, an alternative approach is to enhance the iron content of the milk on which the piglets are feeding by treating the mother pig using oral or parenteral administration, for example with an injectable slow release preparation (such an approach may also be of interest in a human context). When it is applicable to feed piglets on foodstuffs other than the milk of the mother pig, it may also be possible to effect the pharmaceutical administration of the iron complex in this other foodstuff.

Other forms of administration than by injection or through the oral route may also be considered in both human and veterinary contexts, for example the use of suppositories or pessaries for human administration. Another form of pharmaceutical composition of some particular interest is one for buccal or nasal administration and such compositions are discussed hereinafter in more detail.

Compositions may be formulated in unit dosage form, i.e. in the form of discrete portions containing a unit dose, or a multiple or sub-unit of a unit dose. Whilst the dosage of iron complex given will depend on various factors, including the particular compound which is employed in the composition, it may be stated by way of guidance that maintenance of the amount of iron present in the human body at a satisfactory level will often be achieved using a daily dosage, in terms of the iron content of the compound, which lies in a range from about 0.1 to 10 mg and often in a range of from 0.5 to 10 mg, for example 1 or 2 mg, veterinary doses being on a similar g/Kg body weight ratio. However, it will be appreciated that it may be appropriate under certain circumstances to give daily dosages either below or above these levels. In general, the aim should be to provide the amount or iron required by the patient without administering any undue excess and the properties of the pharmaceutical compositions according to the present invention are particularly suited to the achievement of this aim.

It will be appreciated from the foregoing discussion that more than one iron complex according to the present invention may be contained in the pharmaceutical composition, or indeed, other active compounds may be included in the composition, for example compounds having the ability to facilitate the treatment of anaemia, such as folic acid. Another additional component which may be included in the composition, if desired, is a source of zinc. Iron compounds used in the treatment of iron deficiency anaemia can inhibit the mechanism of zinc uptake in the body and this can cause serious side effects in the foetus when treating anaemia in a pregnant female. It is believed, however, that the iron complexes of the present invention have a further advantage in that they either do not have this effect or exhibit the effect at a lower level than the compounds at present used in the treatment of anaemia. Accordingly, it may often be the case that the level of zinc-providing compound added to the composition may not require to be high or, with preferred formulations of the iron complexes, may be dispensed with altogether.

It has never before been appreciated that the novel iron complexes described herein might be used, and with great advantage, in a pharmaceutical context. Accordingly the present invention includes an iron complex as defined hereinbefore for use in medicine, particularly in the treatment of iron anaemia deficiency.

The iron complexes described herein are particularly suited to the treatment of iron anaemia deficiency both in humans and also in a veterinary context, particularly for the treatment of various mammalian species and especially pigs. The complexes will partition into n-octanol indicating that they are able to permeate biological membranes, this property may be confirmed in practice by tests of the ability of the $^{59}$Fe labelled iron complexes to permeate erythrocytes. The ability of the compounds in this respect will depend on the nature of the ligands present therein and the reflection of this ability in the $K_{part}$ values of various compounds has been referred to hereinbefore.

Certain aspects of their formulation may enhance the activity of the iron complexes in particular contexts. Thus, although the neutral ferric complexes containing a 3:1 molar proportion of ligand:iron(III) are of particular value as being stable over a wide pH range from about 4 to 5 up to 10, if administered orally they will dissociate at the pH values of less than 4 prevailing in the stomach to form a mixture of the 2:1 and 1:1 complex together with free ligand. Firstly, one of several variations may be employed which avoid or reduce exposure of the iron complex to the acidic conditions of the stomach. Such approaches may involve various types of controlled release system, ranging from one, which may for example be based on a polymer, which simply provides a delayed release of the complex with time, through a system which is resistant to dissociation under acidic conditions, for example by the use of buffering, to a system which is biased towards release under conditions such as prevail in the small intestine, for example a pH sensitive system which is stabilised towards a pH of 1 to 3 such as prevails in the stomach but not one of 7 to 9 such as prevails in the small intestine. Since the pH of the stomach is higher after a meal, it may be advantageous, whatever method of formulation is used, to administer the iron complexes at such a time.

A particularly convenient approach to a controlled release composition involves encapsulating the iron complex by a material which is resistant to dissociation in the stomach but which is adapted towards dissociation in the small intestine (or possibly, if the dissociation is slow, in the large intestine). Such encapsulation may be achieved with liposomes, phospholipids generally being resistant to dissociation under acidic conditions. The liposomally entrapped 3:1 iron(III) complexes can therefore survive the acid environment of the stomach without dissociating to the 2:1 and 1:1 complexes, and the free hydroxypyrone. On entry into the small intestine the pancreatic enzymes rapidly destroy the phospholipid-dependent structure of the liposomes thereby releasing the 3:1 complex. Liposome disruption is further facilitated by the presence of bile salts. However, it is usually more convenient to effect the encapsulation, including microencapsulation, by the use of a solid composition of a pH sensitive nature.

The preparation of solid compositions adapted to resist dissociation under acidic conditions but adapted towards dissociation under non-acidic conditions is well known in the art and most often involves the use of enteric coating, whereby tablets, capsules, etc. or the individual particles or granules contained therein, are coated with a suitable material. Such procedures are described, for example, in the article entitled "Production of enteric coated capsules" by Jones in Manufacturing Chemist and Aerosol News, May 1970, and in such standard reference books as "Pharmaceutical Dosage Forms", Volume III by Liebermann and Lackmann (published by Marcel Decker). One particular method of encapsulation involves the use of gelatine capsules coated with a cellulose acetate phthalate/diethylphthalate layer. This coating protects the gelatin capsule from the action of water under the acid conditions of the stomach where the coating is protonated and therefore stable. The coating is however destabilised under the neutral/alkaline conditoons of the intestine where it is not protonated, thereby allowing water to act on the gelatin. Once released in the intestine the rate of permeation of the intestine wall by the water soluble 3:1 iron-(III) complex is relatively constant irrespective of the position within the intestine, i.e. whether in the jejunum, ileum or large intestine. Other examples of methods of formulation which may be used include the use of polymeric hydrogel formulations which do not actually encapsulate the iron complex but which are resistant to dissociation under acidic conditions.

A second approach to countering the effect of the acidic conditions prevailing in the stomach, which is described in GB 2117766A and which may also have certain other advantages described therein, is to formulate the iron complex in the pharmaceutical composition together with one or more of the metal-free ligand-providing compounds from which it is derived. Although, this approach may also be considered with the iron complexes of the present invention, particularly when using a metal-free compound of type (1) or (2), it is perhaps rather less attractive in this case in view of the possibility of effecting an exchange between the metal-free compound and the bound ligands, particularly those of type (3) to produce a different type of complex. Also described in GB 2117766A (U.S. Pat. No. 4,550,101) is the use of an iron complex in admixture with a different metal-free iron chelating agent. Once again, this approach may also be considered with the iron complexes of the present invention but is less attractive for similar reasons.

It will be appreciated that the present invention also includes a method for the treatment of a patient to effect an increase in the levels of iron in the patient's bloodstream which comprises administering to said patient an amount of an iron complex as described hereinbefore effective to achieve such an increase.

In addition to the pharmaceutical uses of the iron complexes discussed above they are also of potential interest as a source of iron in various other contexts including in cell and bacterial growth, in plant growth, as a colouring agent and in the control of iron transport across membranes.

This invention is illustrated by the following Examples.

EXAMPLES

Example 1

Preparation of iron complexes (A) An ethanolic solution of ferric chloride is reacted for 5 minutes at room temperature with a chloroform solution containing 2 molar equivalents of maltol (3-hydroxy-2-methyl-4-pyrone) and 1 molar equivalent of 1-ethyl-3-hydroxypyrid-2-one[1]. The resultant solution is neutralised by the addition of solid sodium carbonate with stirring, the precipitated sodium chloride is removed by filtration and the filtrate is evaporated to give, as an oil, an essentially quantitive yield of a mixture of 3:1 complexes in which the (maltol)$_2$ (1-ethyl-3-hydroxypyrid-2-one) iron(III) complex predominates. This oil solidifies on standing to give a glass, $\nu_{max}$(glass) 1525, 1560, 1620, 1645 cm$^{-1}$. (The infra-red spectrum of this compound, and of the other compounds described hereinafter, is obtained by dissolving the original glass in chloroform and evaporating this solution in situ on the sodium chloride plates to re-form a glass on which the infra-red spectrum is run).

[1] The concentration of the 1 molar equivalent ligand-providing compound is ca. 0.1M although this concentration may be varied, for example in a range of 0.1 to 1M, subject only to the solubility of the particular ligand-providing compounds in the solvent system being used.

The neutral ferric complexes of (a) ethylpyromeconic acid (2-ethyl-3-hydroxy-4-pyrone) and maltol and (b) 1-(ethyl-3-hydroxypyrid-2-one and 1-butyl-3-hydroxypyrid-4-one are similarly prepared by procedure (A) to give (a) a mixture of 3:1 complexes in which the (ethylpyromeconic acid)$_2$ (maltol) iron(III) complex predominates, as a glass, and (b) a mixture of 3:1 complexes in which the (1-ethyl-3-hydroxypyrid-2-one)$_2$ (1-butyl-3-hydroxypyrid-4-one) iron(III) complex predominates, as a glass, $\nu_{max}$ 1525, 1530, 1610 cm$^{-1}$.

(B) An ethanolic solution of ferric chloride is treated with a hot (60° C.) ethanolic solution containing 2 molar equivalents of maltol and 1 molar equivalent of ascorbic acid[1] (the use of hot ethanol, rather than cold chloroform as in procedure (A), is required to dissolve the ascorbic acid) and the mixture allowed to cool to room temperature over 30 minutes. The resultant cold solution is neutralised by the addition of solid sodium carbonate with stirring, the precipitated sodium chloride is removed by filtration and the filtrate is evaporated to give, as an oil, an essentially quantitative yield of a mixture of 3:1 complexes in which the (maltol)$_2$ (ascorbic acid) iron(III) complex predominates. This oil solidified on standing to give a glass, $_{max}$ (glass) 1500, 1560, 1600, 1790 cm$^{-1}$.

The neutral ferric complexes of (a) maltol and leucine and (b) maltol and glycine are similarly prepared by procedure (B) to give (a) a mixture of 3:1 complexes which the (maltol)$_2$ (leucine) complex predominates, as a glass, $_{max}$ 1500, 1560, 1595 cm$^{-1}$, and (b) a mixture of 3:1 complexes in which the (maltol)$_2$ (glycine) iron(III) complex predominates, as a glass.

Determination of partition coefficients

The partition coefficient K$_{part}$, being the ratio (concentration of compound in n-octanol)/(concentration of a compound in aqueous phase) on partition between n-octanol and aqueous tris hydrochloride (20 mM, pH 7.4; tris represents 2-amino-2-hydroxymethylpropane 1,3-diol), is measured at 20° C. for the 3:1 iron(III) complexes listed in the Table (at 10$^{-4}$M) by spectophotometry, the complex prepared as described above being dissolved initially in the aqueous tris hydrochloride. Acid washed glassware is used throughout and, following mixing of 5 ml of the 10$^{-4}$M aqueous solution with 5 ml of n-octanol for 1 minute, the aqueous n-octanol mixture is centrifuged at 1,000 g for 30 seconds. The two resulting phases are separated for a concentration determination by spectrophotometry on each, the range 340-640 nm being used. Values typical of those obtained are shown in the Table.

TABLE 1

| Partition coefficients | |
|---|---|
| Iron(III) complex | Partition coefficient |
| (maltol)$_2$(1-ethyl-3-hydroxypyrid-2-one) | 0.32 |
| (ethylpyromeconic acid)$_2$(maltol) | 1.69 |
| (1-ethyl-3-hydroxypyrid-2-one)$_2$ (1-butyl-3-hydroxypyrid-4-one) | 3.56 |
| (maltol)$_2$(ascorbic acid) | 0.14 |
| (maltol)$_2$(leucine) | 0.17 |
| (maltol)$_2$(glycine) | 0.18 |

EXAMPLE 2

Donation of iron to apotransferrin (Maltol)$_2$ (ascorbic acid) iron(III) was prepared in situ by dissolving maltol and ascorbic acid in a 2:1 molar ratio in an aqueous medium containing morpholine propane sulphonate (MOPS, 25 mM) and sodium hydrogen carbonate (30 mM), the pH being adjusted to 7.4 with hydrochloric acid (50% v/v). To the medium was added a solution of $^{59}$Fe enriched ferric chloride in 0.1M aqueous hydrochloric acid containing a molar amount of iron equivalent to that of the ascorbic acid. Equal volumes of the solution of the iron complex and of aportransferrin in the same aqueous medium were mixed to provide concentrations in the mixture of $5\times10^{-5}$M of apotransferrin and $1\times10^{-4}$M of iron.

The mixture was incubated at room temperature in separate experiments for 10 and 60 minutes and an aliquot was then added to a Sephadex G10 column equilibrated with the same aqueous medium described above and the column eluted with that medium, fractions being collected and counted. The percentages of $^{59}$Fe associated with apotransferrin and with the ligands are calaculated as cpm iron-apotransferrin/total cpm and cpm iron-(maltol)$_2$ (ascorbic acid)/total cpm.

It was found that after 10 minutes 43% of the $^{59}$Fe was associated with apotransferrin and 57% of the $^{59}$Fe with the ligands, whilst after 60 minutes the amount of $^{59}$Fe donated to the apotransferrin had risen to 75%, only 25% remaining associated with the ligands.

EXAMPLE 3

In vitro tests on permeation of iron complexes into human erythrocytes

The accumulation of iron by human erythrocytes which are associated with (ethylpyromeconic acid)$_2$ (maltol) iron(III), (maltol)$_2$ (ethylpyromeconic acid) iron(III), (maltol)$_2$ (ascorbic acid) iron(III) and (1-ethyl-3-hydroxypyrid-2-one)$_2$ (1-butyl-3-hydroxypyrid-4-one) iron(III) was studied together with that of a group of four other iron compounds for comparative purposes, this group comprising the 3:1 homogeneous iron complexes, (ethylpyromeconic acid)$_3$ iron(III) and (maltol)$_3$ iron(III), and the salts, ferric NTA (nitrilotriacetic acid) and ferrous sulphate.

The iron compounds were used in solution in an aqueous medium containing tris (20 mM) and sodium chloride (130 mM), the pH being adjusted to 7.4 with hydrochloric acid (50% v/v). The solid ferric NTA and ferric sulphate, labelled with $^{59}$Fe, were dissolved in the aqueous medium to produce a $10^{-4}$M solution whilst the iron complexes were prepared in situ by solution of the ligand-providing compound, or of an appropriate molar ratio of ligand-providing compounds, in the aqueous medium and the addition of an appropriate molar proportion of $^{59}$Fe enriched ferric chloride in 0.1M aqueous hydrochloric acid, the final concentration of iron being $10^{-4}$M.

Packed human erythrocytes (0.5 ml) were incubated in the aqueous medium at 37° C. in separate experiments for 5 and 30 minutes in all cases, and for the (maltol)$_2$ (ascorbic acid) iron(III) complex only, in a series of experiments conducted for 2, 5, 10, 15, 30, 45 and 60 minutes. Following incubation, an aliquot of the erythrocyte incubation medium mixture was separated by centrifugation over two layers of silicone oil ($\rho=1.07$, and $\rho=1.2$ respectively. The $^{59}$Fe levels associated with each of the erythrocytes and the incubation medium were counted and are presented as a distribution ratio (concentration in erythrocytes/concentration in medium) in Table 2 for the 5 and 30 minute experiments and in Table 3 for the other experiment with (maltol)$_2$ (ascorbic acid) iron(III) (all data in the Tables represents a mean of at least three independent experiments).

It will be seen from Table 2 that ethylpyromeconic acid is more effective as a ligand than maltol in producing uptake of an iron complex by erythrocytes, the uptake both for the complex containing three ethylpyromeconic acid ligands and that containing two of such ligands reaching an equilibrium after only 5 minutes. It should also be noted that a higher level of iron uptake is achieved at 30 minutes for each of the three mixed ligand complexes containing a hydroxypyrone ligand than for either of the complexes containing three identical hydroxypyrone ligands.

TABLE 2

| Compound | Ligand concentration (mM) | Distribution ratio 5 minutes | Distribution ratio 30 minutes |
|---|---|---|---|
| $Fe^{III}$(ethylpyromeconic acid)$_3$ | 0.3 | 3.7 | 3.6 |
| $Fe^{III}$(maltol)$_3$ | 0.3 | 0.2 | 1.1 |
| $Fe^{III}$(ethylpyromeconic acid)$_2$ maltol | 0.2:0.1 | 5.6 | 5.2 |
| $Fe^{III}$(maltol)$_2$(ethylpyromeconic acid) | 0.2:0.1 | 1.9 | 6.3 |
| $Fe^{III}$(maltol)$_2$(ascorbic acid) | 0.2:0.1 | 1.5 | 5.2 |
| $Fe^{III}$(1-ethyl-3-hydroxypyrid-2-one)$_2$(1-butyl-3-hydroxypyrid-4-one) | 0.2:0.1 | 0.4 | 1.4 |
| $Fe^{III}$NTA | 0.1 | 6.2 | 4.9[1] |
| $Fe^{II}SO_4$ | 0.1 | 5.0 | 4.3[1] |

[1] An analysis of the erythrocyte membranes after incubation shows that these apparently high levels of iron uptake are due to binding to the cell membrane and do not in fact reflect true values of iron uptake.

TABLE 3

| [$Fe^{III}$(maltol)$_2$(ascorbic acid)] | |
|---|---|
| Time (minutes) | Distribution ratio |
| 2 | 6.1 |
| 5 | 8.0 |
| 10 | 10.2 |
| 15 | 12.2 |
| 30 | 17.1 |
| 45 | 26.5[1] |
| 60 | 30.8[1] |

[1] These high values arise from dissociation of the complex and donation of iron to intracelluar protein.

EXAMPLE 4

In vitro tests experimention of non-everted rat jejunal segments by iron complexes The uptake of iron by non-everted rat jejunal segments was studied for (ethylpyromeconic acid)$_2$ (maltol) iron(III), (maltol)$_2$ (ethylpyromeconic acid) iron(III) and (1-ethyl-3-hydroxypyrid-2-one)$_2$ (1-butyl-3-hydroxypyrid-4-one) iron(III). For comparative purposes, similar experiments were carried out with (ethylpyromeconic acid)$_3$ iron(III) and (maltol)$_3$ iron(III), the latter complex being used alone and in admixture with an excess of maltol corresponding to either 1 molar proportion or 7 molar proportions of free maltol in addition to the 3 molar proportions contained in the complex in association with 1 molar proportion of iron(III).

The iron complexes were prepared in situ in oxygenated HEPES buffer by solution of the appropriate amount of the ligand-providing compound, or of an appropriate molar ratio of ligand-providing compounds, in the buffer and the addition of an appropriate molar proportion of $^{59}$Fe enriched ferric chloride in 0.1M aqueous hydrochloric acid, the final concentration of iron being $10^{-4}$M.

Rats (male, Sprague Dawley, 70-90 g) were killed and the jejunum removed. It was divided into 3 cm lengths, each being cut lengthwise and opened out. These lengths were further cut into segments of 30-35 mg (3 per incubation flask). The jejunum was incubated at 37° C. (pre-incubated flasks being used, each of which contained 3 segments) in a medium of oxygenated HEPES buffer containing the appropriate iron complex for 10 minutes. The tissue and medium were then counted.

The uptake of $^{59}$Fe was calculated as a distribution ratio (concentration in tissue/concentration in medium) corrected for the water content (80%) and the extracellular fraction (found to be 20% by sulphate space studies) of the tissue. The results are shown in Table 4 and it will be seen, in contrast to the results obtained with erythrocytes, that the uptake of iron from the complex containing three ethylpyromeconic acid ligands is not greater than that for the complex containing three maltol ligands. However as in the erythrocyte experiments, the uptake of iron is greater for the three mixed ligand complexes containing a hydroxypyrone ligand than for either of the complexes containing three hydroxypyrone ligands.

TABLE 4

| Compound | Ligand concentration (mM) | Distribution ratio |
|---|---|---|
| Fe$^{(III)}$(maltol)$_3$ + maltol (1:7 molar ratio of complex: maltol) | 1 | 0.1 |
| Fe$^{(III)}$(maltol)$_3$ + maltol (1:1 molar ratio of complex: maltol) | 0.4 | 0.6 |
| Fe$^{(III)}$(maltol)$_3$ | 0.3 | 1.3 |
| Fe$^{(III)}$(ethylpyromeconic acid)$_3$ | 0.3 | 1.0 |
| Fe$^{(III)}$(ethylpyromeconic acid)$_2$(maltol) | 0.2:0.1 | 6.0 |
| Fe$^{(III)}$(maltol)$_2$(ethylpyromeconic acid) | 0.2:0.1 | 4.3 |
| Fe$^{(III)}$(maltol)$_2$(ascorbic acid) | 0.2:0.1 | 9.7 |
| Fe$^{(III)}$(1-ethyl-3-hydroxypyrid 2-one)$_2$-(1-butyl-3-hydroxy-pyrid-4-one) | 0.2:0.1 | 2.4 |

We claim:

1. A pharmaceutical composition suitable for increasing the level of iron in a patient's bloodstream, comprising:
(A) a physiologically effective amount of a neutral 3:1 iron complex containing three monobasic, bidentate ligands, of which at least two are different, in combination with a ferric cation, each ligand separately being provided by a compound being:
  (1) 3-hydroxy-4-pyrone or a 3-hydroxy-4-pyrone in which one or more of the hydrogen atoms attached to ring carbon atoms are replaced by a C$_{1-4}$ aliphatic or alicyclic hydrocarbon group;
  (2) a 3-hydroxypyrid-2-one or 3-hydroxypyrid-4-one in which (a) the hydrogen atom attached to the nitrogen atom of the 3-hydroxypyridone ring is replaced by a formyl, alkylcarbonyl, cycloalkylcarbonyl, C$_{1-6}$ aliphatic or alicyclic hydrocarbon group, or a C$_{1-8}$ aliphatic or alicyclic hydrocarbon group substituted by one or two substituents selected from formyl, alkylcarbonyl, cycloalkylcarbonyl, alkoxy, aliphatic amido, alicyclic amido, halo, hydroxy and aliphatic or alicyclic hydrocarbylcarbonyloxy, hydrocarbylsulphonyloxy, hydrocarbyloxycarbonyl or hydrocarbyloxysulphonyl, and (b) wherein one or more of the hydrogen atoms attached to the carbon atoms of the 3-hydroxypyridone ring can be replaced by one of said substituents, by a C$_{1-6}$ aliphatic or alicyclic hydrocarbon group, or by a C$_{1-8}$ aliphatic or alicyclic hydrocarbon group substituted by alkoxy, halo, hydroxy or aliphatic or alicyclic hydrocarbylcarbonyloxy, hydrocarbylsulphonyloxy, hydrocarbyloxycarbonyl or hydrocarbyloxysulphonyl; or
  (3) a compound selected from the group consisting of formic acid, acetic acid, propionic acid, lactic acid, gluconic acid, ascorbic acid, glycine, isoleucine, leucine, methionine, phenylalanine, tyrosine and valine;
said compound of type (1), (2) or (3) when metal free having a partition coefficient at 20° C. between n-octanol and 20 mM tris hydrochloride, pH 7.4, of above 0.02 but less the 3.0 for the ratio (concentration of compound in organic phase)/(concentration of compound in aqueous phase), and with the proviso that at least one of the ligands is provided by a compound of type (1) or (2); and
(B) a physiologically acceptable diluent or carrier.

2. A pharmaceutical composition according to claim 1, in which at least one ligand is provided by a compound of type (1).

3. A pharmaceutical composition according to claim 1, in which each ligand is provided by a compound of type (1).

4. A pharmaceutical composition according to claim 3, in which the compound of type (1) is 3-hydroxy-4-pyrone or a 3-hydroxy-4-pyrone in which one or more of the hydrogen atoms attached to ring carbon atoms is replaced by the same or a different substituent selected from methyl, ethyl, n-propyl and isopropyl groups.

5. A pharmaceutical composition according to claim 2, in which the compound is of type (1) and is 3-hydroxy-3-methyl-4-pyrone or 2-ethyl-3-hydroxy-4-pyrone.

6. A pharmaceutical composition according to claim 1, in solid form.

7. A pharmaceutical composition suitable for increasing the level of iron in a patient's bloodstream, comprising a physiologically effective amount of a neutral 3:1 iron complex containing three monobasic, bidentate ligands, of which at least two are different, in combination with a ferric cation, each ligand separately being provided by a compound being:
  (1) 3-hydroxy-4-pyrone or a 3-hydroxy-4-pyrone in which one or more of the hydrogen atoms attached to ring carbon atoms are replaced by a C$_{1-4}$ aliphatic or alicyclic hydrocarbon group;
  (2) a 3-hydroxypyrid-2-one or 3-hydroxypyrid-4-one in which (a) the hydrogen atom attached to the nitrogen atom of the 3-hydroxypyridone ring is replaced by a formyl, alkylcarbonyl, cycloalkylcarbonyl, C$_{1-6}$ aliphatic or alicyclic hydrocarbon group, or a C$_{1-8}$ aliphatic or alicyclic hydrocarbon group substituted by one or two substituents selected from formyl, alkylcarbonyl, cycloalkylcarbonyl, alkoxy, aliphatic amido, alicyclic amido, halo, hydroxy and aliphatic or alicyclic hydrocarbylcarbonyloxy, hydrocarbylsulphonyloxy, hydrocarbyloxycarbonyl or hydrocarbyloxysulphonyl, and (b) wherein one or more of the hydrogen atoms attached to carbon atoms of the 3-hydroxypyridone ring can be replaced by one of said substituents, by a C$_{1-6}$ aliphatic or alicyclic hydrocarbon group, or by a C$_{1-8}$ aliphatic or alicyclic hydrocarbon group substituted by alkoxy, halo, hydroxy or aliphatic or alicyclic hydrocarbylcarbonyloxy, hydrocarbylsulphonyloxy, hydrocarbyloxycarbonyl or hydrocaryloxysulphonyloxy; or (3) a compound selected from the group consisting of formic acid, acetic acid, propionic acid, lactic acid, gluconic acid, ascorbic acid, glycine, isoleucine, leucine, methionine, phenylalanine, tyrosine and valine;

said compound of type (1), (2) or (3) when metal free having a partition coefficient at 20° C. between n-octanol and 20 mM tris hydrochloride, pH 7.4, of above 0.02 but less the 3.0 for the ratio (concentration of compound in organic phase)/(concentration of compound in aqueous phase), with the proviso that at least one of the ligands is provided by a compound of type (1) or (2), and wherein the said neutral 3:1 iron complex contains 10% by weight or less of any 1:1 or 2:1 iron (III) complex in which the ligand or ligands are selected from those present in the 3:1 complex.

8. A pharmaceutical composition according to claim 1, in which at least two of the ligands are provided by compounds of different types among (1), (2) and (3).

9. A pharmaceutical composition according to claim 3, in which the complex is (3-hydroxy-2-methyl-4-pyrone)$_2$(2-ethyl-3-hydroxy-4-pyrone) iron (III), (2-ethyl-3-hydroxy-4-pyrone)$_2$(3-hydroxy-2-methyl-4-pyrone) iron (III), or a mixture thereof.

10. A pharmaceutical composition according to claim 1, which contains 10% by weight or less of any metal free compound corresponding to a ligand present in the complex.

11. A pharmaceutical composition according to claim 1, in which the compound of type (3) is selected from the group consisting of gluconic acid, ascorbic acid, glycine and leucine.

12. A pharmaceutical composition according to claim 1, in which the compound of type (2) is a 3-hydroxypyrid-2-one in which the hydrogen atom attached to the nitrogen atom of the 3-hydroxypyridone ring is replaced by a $C_{1-6}$ aliphatic or alicyclic hydrocarbon group and, optionally, in which one or more of the hydrogen atoms attached to ring carbon atoms are replaced by the same or a different $C_{1-6}$ aliphatic or alicyclic hydrocarbon group.

13. A method for increasing the level of iron in a patient's bloodstream, said method comprising the step of administering to said patient an amount effective to achieve said increase of a 3:1 neutral iron complex comprising three monobasic, bidentate ligands, of which at least two are different, in combination with a ferric cation, the ligands each separately being provided by a compound being:
 (1) 3-hydroxy-4-pyrone or a 3-hydroxy-4-pyrone in which one or more of the hydrogen atoms attached to ring carbon atoms are replaced by a $C_{1-4}$ aliphatic or alicyclic hydrocarbon group;
 (2) a 3-hyroxypyrid-2-one or 3-hydroxypyrid-4-one in which (a) the hydrogen atom attached to the nitrogen atom of the 3-hydroxypyridone ring is replaced by a formyl, alkylcarbonyl, cycloalkylcarbonyl, $C_{1-6}$ aliphatic or alicyclic hydrocarbon group, or a $C_{1-8}$ aliphatic or alicyclic hydrocarbon group substituted by one or two substituents selected from formyl, alkylcarbonyl, cycloalkylcarbonyl, alkoxy, aliphatic amido, alicyclic amido, halo, hydroxy and aliphatic or alicyclic hydrocarbylcarbonyloxy, hydrocarbylsulphonyloxy, hydrocarbyloxycarbonyl or hydrocarbyloxysulphonyl, and (b) wherein one or more of the hydrogen atoms attached to the carbon atoms of the 3-hydroxypyridone ring can be replaced by one of said substituents, by a $C_{1-6}$ aliphatic or alicyclic hydrocarbon group, or by a $C_{1-8}$ aliphatic or alicyclic hydrocarbon group substituted by alkoxy, halo, hydroxy or aliphatic or alicyclic hydrocarbylcarbonyloxy, hydrocarbylsulphonyloxy, hydrocarbyloxycarbonyl or hydrocarbyloxysulphonyl; or
 (3) a compound selected from the group consisting of formic acid, acetic acid, propionic acid, lactic acid, gluconic acid, ascorbic acid, glycine, isoleucine, leucine, methionine, phenylalanine, tyrosine and valine;

said compound of type (1), (2) or (3) when metal free having a partition coefficient at 20° C. between n-octanol and 20 mM tris hydrochloride, pH 7.4, of above 0.02 but less the 3.0 for the ratio (concentration of compound in organic phase)/(concentration of compound in aqueous phase), and with the proviso that at least one of the ligands is provided by a compound of type (1) or (2).

14. A method according to claim 13, in which at least one ligand is provided by a compound of type (1).

15. A method according to claim 13, in which the compound of type (1) is 3-hydroxy-2-methyl-4-pyrone or 2-ethyl-3-hydroxy-4-pyrone.

16. A method according to claim 13, in which the complex is administered in the form of a composition containing the complex together with a physiologically acceptable solid carrier.

17. A method for increasing the level of iron in a patient's bloodstream, said method comprising the step of administering to said patient an amount effective to achieve said increase of a neutral 3:1 iron complex containing three monobasic, bidentate ligands, of which at least two are different, in combination with a ferric cation, each ligand separately being provided by a compound being:
 (1) 3-hydroxy-4-pyrone or a 3-hydroxy-4-pyrone in which one or more of the hydrogen atoms attached to ring carbon atoms are replaced by a $C_{1-4}$ aliphatic or alicyclic hydrocarbon group;
 (2) a 3-hyroxypyrid-2-one or 3-hydroxypyrid-4-one in which (a) the hydrogen atom attached to the nitrogen atom of the 3-hydroxypyridone ring is replaced by a formyl, alkylcarbonyl, cycloalkylcarbonyl, $C_{1-6}$ aliphatic or alicyclic hydrocarbon group, or a $C_{1-8}$ aliphatic or alicyclic hydrocarbon group substituted by one or two substituents selected from formyl, alkylcarbonyl, cycloalkylcarbonyl, alkoxy, aliphatic amido, alicyclic amido, halo, hydroxy and aliphatic or alicyclic hydrocarbylcarbonyloxy, hydrocarbylsulphonyloxy, hydrocarbyloxycarbonyl or hydrocarbyloxysulphonyl, and (b) wherein one or more of the hydrogen atoms attached to the carbon atoms of the 3-hydroxypyridone ring can be replaced by one of said substituents, by a $C_{1-6}$ aliphatic or alicyclic hydrocarbon group, or by a $C_{1-8}$ aliphatic or alicyclic hydrocarbon group substituted by alkoxy, halo, hydroxy or aliphatic or alicyclic hydrocarbylcarbonyloxy, hydrocarbylsulphonyloxy, hydrocarbyloxycarbonyl or hydrocarbyloxysulphonyl; or
 (3) a compound selected from the group consisting of formic acid, acetic acid, propionic acid, lactic acid, gluconic acid, ascorbic acid, glycine, isoleucine, leucine, methionine, phenylalanine, tyrosine and valine;

said compound of type (1), (2) or (3) when metal free having a partition coefficient at 20° C. between n-octanol and 20 mM tris hydrochloride, pH 7.4, of above 0.02 but less the 3.0 for the ratio (concentration of compound in organic phase)/(concentration of compound in aqueous phase), with the proviso that at least one of the ligands is provided by a compound of type (1) or (2), and wherein the said neutral 3:1 iron complex contains 10% by weight or less of any 1:1 or 2:1 iron (III) complex in which the ligand or ligands are selected from those present in the 3:1 complex.

18. A method according to claim 13, in which the complex is (3-hydroxy-2-methyl-4-pyrone)$_2$(2-ethyl-3-hydroxy-4-pyrone) iron (III), (2-ethyl-3-hydroxy-4-pyrone)$_2$(3-hydroxy-2-methyl-4-pyrone) iron (III), or a mixture thereof.

19. A method for increasing the level of iron in a patient's bloodstream, said method comprising the step of administering to said patient an amount of effective to achieve said increase of a pharmaceutical composition according to claim 3, 4, 8, 10, 11 or 12.

* * * * *

UNITED STATES PATENT AND TRADEMARK OFFICE
CERTIFICATE OF CORRECTION

PATENT NO. : 5,177,068
DATED : January 5, 1993
INVENTOR(S) : CALLINGHAM ET AL It is certified that error appears in the above-identified patent and that said Letters Patent is hereby corrected as shown below:

On the title page, Item [19]
"Callingham et al" appearing below "United States Patent"
and insert --Hider et al--

Item [75] delete "Brian A. Callingham, Cambridge;"
Column 6 line 20, delete the incomplete formula and replace by:

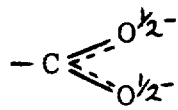

Column 18 lines 30-31, delete "3-hydroxy-3-methyl-4-pyrone"
and replace by -- 3-hydroxy-2-methyl-4-pyrone" --

Signed and Sealed this

First Day of March, 1994

*Attest:*

BRUCE LEHMAN

*Attesting Officer*   *Commissioner of Patents and Trademarks*